United States Patent
Panov et al.

(10) Patent No.: US 7,105,704 B2
(45) Date of Patent: Sep. 12, 2006

(54) METHOD FOR PRODUCING MONOCYCLIC KETONES $C_7$-$C_{20}$

(75) Inventors: Gennady Ivanovich Panov, Novosibirsk (RU); Constantin Alexandrovich Dubkov, Novosibirsk (RU); Eygeny Vladimirovich Starokon, Berdsk (RU); Dmitry Petrovich Ivanov, Novosibirsk (RU)

(73) Assignee: Institut Kataliza Imeni G.K. Boreskova Sibirskogo Otdeleniya Rossiiskoi Akademii Nauk, (RU)

( * ) Notice: Subject to any disclaimer, the term of this patent is extended or adjusted under 35 U.S.C. 154(b) by 0 days.

(21) Appl. No.: 10/508,366

(22) PCT Filed: Nov. 6, 2002

(86) PCT No.: PCT/RU02/00492

§ 371 (c)(1),
(2), (4) Date: Apr. 13, 2005

(87) PCT Pub. No.: WO03/078375

PCT Pub. Date: Sep. 25, 2003

(65) Prior Publication Data

US 2005/0203316 A1    Sep. 15, 2005

(30) Foreign Application Priority Data

Mar. 20, 2002    (RU) ............................. 2002106987

(51) Int. Cl.
*C07C 49/307*    (2006.01)
*C07C 45/27*    (2006.01)
(52) U.S. Cl. ....................................... 568/375; 568/363
(58) Field of Classification Search ................... None
See application file for complete search history.

(56) References Cited

U.S. PATENT DOCUMENTS 3,419,615 A    12/1968    Inchalik et al.
3,917,708 A    11/1975    Kuessner et al.

FOREIGN PATENT DOCUMENTS

GB    649680    1/1951
GB    930842    7/1963
SU    504749 A    6/1976

OTHER PUBLICATIONS

Bridson-Jones et al., Oxidation of Organic Compounds by Nitrous Oxide, in J.Chem.Soc., Nov. 1951; pp. 2999, 3001, 3004, 3008.
Pannetier, G., et al. "Regions of flammability of binary mixtures of hydrocarbons with nitrous oxide: Action of nitrous oxide as oxidant" *Fifth Symposium on Combustion* (1955) pp. 620-928.
Brandt, B.B., et al. "Firing limits for $N^2O$ mixtures with inflammable gases and vapours" *Khimicheskaya Phomyshlennost* (1960) No. 5, pp. 67-73. Partial English translation of p. 67, pp. 69-72.

*Primary Examiner*—Sikarl A. Witherspoon
(74) *Attorney, Agent, or Firm*—Ladas and Parry LLP

(57) ABSTRACT

The invention relates to a method for producing monocyclic ketones $C_7$–$C_{20}$.

The method of patent protection sought is based on the oxidation reaction of monocyclic alkenes $C_7$–$C_{20}$ into corresponding monocyclic ketones with nitrous oxide or a mixture thereof with inert gas. The process proceeds at a temperature ranging from 20 to 350° C. and a pressure of the nitrous oxide ranging from 0.01 to 100 atm.

The process provides a high selectivity involving the target product, blast-resistant work operations and is promising for industrial use.

10 Claims, No Drawings

METHOD FOR PRODUCING MONOCYCLIC KETONES $C_7$-$C_{20}$

FIELD OF THE INVENTION

This application is the national stage of PCT/RU02/00492, filed Nov. 16, 2005, and published as WO 03/078375 on Sep. 29, 2003.

The invention relates to a method for producing monocyclic ketones $C_7$–$C_{20}$, more particularly, the method for producing same by the liquid-phase oxidation with nitrous oxide ($N_2O$), of monocyclic alkenes of the formula $C_nH_{2n-2}$ containing 7–20 carbon atoms.

Monocyclic ketones $C_7$–$C_{20}$ are the most significant intermediate products in synthesis of variegated organic compounds, with dicarboxylic acids and lactams among them. The latter are employed for the production of various polyamide materials, for example, Nylon-8, Nylon-12, to mention only few.

BACKGROUND OF THE INVENTION

The main method for producing monocyclic ketones is the liquid-phase oxidation of corresponding cycloalkanes with atmospheric oxygen, which oxidation can be carried out in the presence of a catalyst and without it. In both cases, the reaction products formed are represented by a mixture of cyclic ketones and alcohols. For example, while oxidizing cyclododecanes at a temperature comprised between 155 and 170° and a pressure of between 1 and 10 atm, in the presence of boric acid, a mixture of cyclododecanones and cyclododecanols is formed having an ultimate selectivity of about 90%, an obtainable conversion between 5 and 20%/ U.S. Pat. No 3,419,615 CO7C 29/52, 1968/ and, along with this, a selectivity involving the ketone does not exceed 20%. The oxidation of cyclododecanes into a mixture of cyclododecanones and cyclododecanols can likewise be carried out with employment, as catalysts, of Co or Mn salts at a temperature comprised between 90 and 150°/GB Pat. No 930842, CO7C, 1963/. In patent U.S. Pat. No 3,917,708, CO7C 29/50, 1975 there is shown and described a method for oxidizing cyclic alkanes $C_5$–$C_{12}$ into a mixture of corresponding cyclic ketones and alcohols, in the presence of Co, Mn, Cu, Fe, Ni salts. The process is conducted at 130–160° C., a pressure of between 5 and 25 atm and a conversion of between 3 and 6%.

The common defect of these methods is formation, alongside ketones, of appreciable amounts of cyclic alcohols and also a drastic reduction in a reaction selectivity, as the conversion is increased.

In patent GB No 649680, CO7C 45/34, 1951, a disclosure is made of a method for oxidizing olefins into carbonyl compounds with nitrous oxide. According to this method, it is particularly possible to obtain cyclooctanones by the oxidation of cyclooctenes. This method is disadvantageous in low selectivity and stringent reaction conditions.

A second serious disadvantage of this method is a possibility of ignitable mixtures being formed. For explosion hazard to be precluded, the authors of the patent propose adding further saturated hydrocarbons to a reaction mixture. However, as shown by later research work, the mixtures of saturated hydrocarbons with $N_2O$ are nearly as much dangerously explosive as those of olefins /G. Panetier, A. Sicard, V Symposium on Combustion, 620, 1955; B. B. Brandt, L. A. Matov, A. I. Rozlovsky, V. S. Khailov, Khim. Prom. 1960, No 5, pp. 67–73/. Therefore, the saturated hydrocarbons, despite their lesser reactivity, cannot be a means for precluding the explosion hazard.

SUMMARY OF THE INVENTION

The invention protects a method for producing monocyclic ketones $C_7$–$C_{20}$ by way of oxidizing monocyclic alkenes, which is devoid of said disadvantages.

According to this method, in order to obtain an enhanced selectivity, a reaction is conducted under milder conditions when an alkene is present in the form of a liquid phase, in which the oxidation reaction proceeds with a high selectivity. An excessive rise in temperature and/or pressure of $N_2O$ is unwanted because it can lead to a selectivity reduced on account of the contribution of gas-phase oxidation.

Explosion-proof work conditions according to the claimed method, are secured by the addition of an inert gas to a reaction mixture not allowed to react with $N_2O$, for example nitrogen, argon, helium, carbon dioxide, to mention but few, or a mixture thereof. The role of the inert gas can be played by reaction exhaust gases. At various process stages, depending on an alkene: nitrous oxide ratio, a portion of the inert gas required for providing explosion-proof operations may vary and be produced by its separate supply. From the viewpoint of simplicity and the maximum safety of the process, it can be advantageous to have the nitrous oxide diluted with the inert gas such that the reaction mixture is explosion-proof with any content of cyclohexane. This condition is fulfilled providing an $N_2O$ content in admixture with the inert gas is not more than 25%. The use of this mixture precludes dangerously explosive situations to evolve at all the process stages.

For explosion hazard to be reduced, a reaction mixture can be added with combustion inhibitors, such as trifluorobromomethane, difluorochlorobromomethane, dibromotetrafluoroethane and so on, and so forth.

In accordance with the present invention, the oxidation of monocyclic alkenes into ketones can be carried out in a wide range of conditions both in a static and a flow reactor which can be made of steel, titanium or other appropriate material. And use can be made of all known technological steps to enhance the efficiency of gas-liquid reactions.

In the case of the static variant of a method, an autoclave is loaded with monocyclic alkenes at room temperature in amounts such that on heating to reaction temperature, it is present in the form of a liquid phase, followed by nitrous oxide or its mixture to be fed with inert gas to bring pressure to a specified value. The quantity of nitrous oxide is selected in such a way as to provide its pressure at reaction temperature to account for 0.01 to 100 atm. The reaction vessel is then closed to be heated to reaction temperature in a range of between 20 and 350° C. Reaction time is selected in relation to reaction conditions and the requirements imposed on process indices; it can vary from several minutes to several dozen hours.

The claimed method can be carried out without solvents. However, it is also possible to perform a process with the use of solvents selected from a wide range of agents to be applied in organic synthesis. The reaction proceeds at a sufficiently high rate without a catalyst, albeit it can be carried out in the presence of said catalyst.

The method claimed for producing monocyclic ketones does not call for a high purity of initial reagents. For example, nitrous oxide can be used both in a pure form and with admixtures of various gases not making a harmful impact on process indices. Monocyclic alkenes $C_7$–$C_{20}$ may likewise contain admixtures of other organic compounds, especially as these do not have double bonds C=C.

The concept of the invention, as being claimed and as set forth in the application, is exemplified in the following manner.

EXAMPLES 1–9

The results of these examples are tabulated (Table I) to show a high selectivity of the liquid phase oxidation reaction of monocyclic alkenes $C_7$–$C_{20}$ into cyclic ketones, with nitrous oxide used as oxidant.

Example I. The reaction vessel, 100 cm³, made of stainless steel and provided with a stirrer (the firm Parr) is filled in with 25 cm³ of cyclooctene (Aldrich, 99%). The reaction vessel is blown down with nitrous oxide to bring its pressure to 25 atm. The reaction vessel is closed in a pressure tight manner, heated to 250° and maintained under this temperature for 3 hours. Upon termination of the reaction, the reaction vessel is cooled to room temperature, pressure is measured and the final composition of gas and liquid phases is analyzed by gas chromatography methods, chromato-mass-spectrometry and NMR. Calculated from the obtainable results is a conversion on cyclooctene (X) and a reaction selectivity involving the cyclooctanone (S):

$$X = \frac{C_{C_8H_{14}O} + \sum C_{side}}{C^0_{C_8H_{14}}} \cdot 100(\%) \quad (1)$$

$$S = \frac{C_{C_8H_{14}O}}{C_{C_8H_{14}O} + \sum C_{side}} \cdot 100(\%), \quad (2)$$

wherein $C^o_{C_8H_{14}}$—initial concentration of cyclooctene; $_{8H\,14\,O}$—concentration of cyclooctanone in reaction products; $C_{side}$—total concentration of by-products. In the case of large conversions, value X can also be calculated according to the difference between the initial and final concentrations of cyclooctene:

$$X = \frac{C^0_{C_8H_{14}} - C_{C_8H_{14}}}{C^0_{C_8H_{14}}} \cdot 100(\%) \quad (3)$$

Example 2 is similar to Example I, with the difference that an experiment is made at 220° for 12 hours.

Example 3 is similar to Example 2, with the difference that an experiment is made at 198° C.

Example 4 is similar to Example 3, with the difference that an experiment is made for 3 hours.

Example 5 is similar to Example 3, with the difference that an experiment is made at 180° C.

Example 6 is similar to Example 3, with the difference that an experiment is made at 150° C.

Example 7 is similar to Example 5, with the difference that cycloheptene is employed instead of cyclooctene.

Example 8 is similar to Example 7, with the difference that the initial pressure of $N_2O$ ($P^o{}_{2O}$) is equal to 15 atm and an experiment is made at 310° for 3 hours.

Example 9 is similar to Example I, with the difference that cyclododecene is employed instead of cyclooctene.

TABLE I

| Example | Cycloalkene | T (° C.) | Time (hr) | X (%) | S (%) |
|---|---|---|---|---|---|
| 1 | Cyclooctene | 250 | 3 | 60 | 95 |
| 2 | Cyclooctene | 220 | 12 | 56.5 | 96 |
| 3 | Cyclooctene | 198 | 12 | 32.7 | 97.5 |
| 4 | Cyclooctene | 198 | 3 | 7.0 | 98 |
| 6 | Cyclooctene | 150 | 12 | 3.3 | 96 |
| 7 | Cycloheptene | 180 | 12 | 12.5 | 97 |
| 8 | Cyclooctene | 310 | 2 | 35 | 95 |
| 9 | Cyclododecene | 250 | 3 | 22 | 96 |

EXAMPLE 10

This is a comparative example. An experiment is made in a way similar to Example I, with the difference that 3 ml of cyclooctene are fed into a reaction vessel, with all of the cyclooctene under reaction conditions in the gas phase. As a result of experiment, a conversion of cyclooctene was below 1%, which goes to show that under these conditions, the gas-phase reaction does not practically take place.

EXAMPLES 11–12

These Examples compared to Examples 2 and 4 demonstrate the influence exerted by the concentration of nitrous oxide on process indices (Table 2). Said concentration in a reaction mixture is specified by the value of its initial pressure at room temperature, $P^o{}_{N2O}$.

Example 11 is similar to Example 2, with the difference that the initial equilibrium pressure of nitrous oxide in this experiment is specified 5 atm.

Example 12 is similar to Example 4, with the difference that the initial equilibrium pressure of nitrous oxide in this experiment is specified 40 atm.

TABLE 2

| Example | $P^o{}_{N2O}$ (atm) | T (° C.) | Time (hr) | X (%) | S (%) |
|---|---|---|---|---|---|
| 2 | 25 | 220 | 12 | 56.5 | 96 |
| 11 | 5 | 220 | 12 | 14 | 97 |
| 4 | 25 | 198 | 3 | 7.0 | 98 |
| 12 | 40 | 198 | 3 | 11.5 | 97.5 |

EXAMPLE 13–14

These Example (Table 3) illustrate a possibility of a process being conducted in the presence of a catalyst.

Example 13 is similar to Example 5, with the difference that the reaction is carried out for 6 hours, in the presence of 0.2 g $Fe_2O_3/SiO_2$ (2.8 wt % of $Fe_2O_3$). A catalyst is prepared by saturating $SiO_2$ with a $FeCl_3$ solution, drying at 110° and calcining in air at 500° for 2 hours.

Example 14 is similar to Example 5, with the difference that the reaction is carried out for 5 hours in the presence of 0.5 g $Ag/SiO_2$ (I wt % of Ag). A catalyst is prepared by saturating $SiO_2$ with an $AgNO_3$ solution, drying at 110° and calcining in air at 500° for 2 hours.

TABLE 3

| Example | Catalyst | T (° C.) | Time (hr) | X (%) | S (%) |
|---------|----------|----------|-----------|-------|-------|
| 13 | $Fe_2O_3/SiO_2$ | 180 | 6 | 8.5 | 94 |
| 14 | $Ag/SiO_2$ | 180 | 5 | 7.0 | 95.5 |

EXAMPLES 15–18

These Examples demonstrate the possibility to oxidize cyclooctenes in the presence of various solvents (Table 4).

Example 15 is similar to Example 5, with the difference that 25 ml of a cyclooctene/cyclohexane mixture are poured into a reaction vessel in a volume ratio of 1:1.

Example 16 is similar to Example 15, with the difference that acetonitrile is used in place of cyclohexane.

Example 17 is similar to Example 15, with the difference that an iso-butyl alcohol is used in place of cyclohexane.

Example 18 is similar to Example 15, with the difference that cyclooctane is used in place of cyclohexane.

TABLE 4

| Example | Solvent | T (° C.) | X (%) | S (%) |
|---------|---------|----------|-------|-------|
| 15 | Cyclohexane | 180 | 13 | 96 |
| 16 | Acetonitrile | 180 | 13.5 | 97 |
| 17 | Iso-butanol | 180 | 10 | 97.5 |
| 18 | Cyclooctane | 180 | 12 | 98 |

EXAMPLES 19–24

These Examples illustrate the possibility to carry out a reaction with nitrous oxide diluted mixtures (Table 5).

Example 19 is similar to Example I, with the difference that a reaction vessel is filled up with, instead of pure nitrous oxide, its mixture with an inert gas—nitrogen, in which the concentration of $N_2O$ is 70%. The initial pressure of the mixture in the reaction vessel $P°$ is 45 atm.

Example 20 is similar to Example 19, with the difference that the concentration of $N_2O$ in mixture with nitrogen is 40% and the initial pressure in the mixture is 40 atm.

Example 21 is similar to Example 19, with the difference that the concentration of $N_2O$ in mixture with nitrogen is 20%. The initial pressure is 90 atm. An experiment is made at 220° C. for 12 hours.

Example 22 is similar to Example 21, with the difference that the initial pressure in a reaction vessel is 45 atm.

Example 23 is similar to Example 21, with the difference that a reaction vessel is supplied with a nitrous oxide/argon mixture, in which the concentration of $N_2O$ is 50%. The initial pressure in the reaction vessel is 30 atm.

Example 24 is similar to Example 23, with the difference that carbon dioxide is used in place of argon.

TABLE 5

| Example | Inert gas | P° (atm) | Concentration of $N_2O$ in mixture (%) | T (° C.) | Time (hr) | X (%) | S (%) |
|---------|-----------|----------|----------------------------------------|----------|-----------|-------|-------|
| 19 | $N_2$ | 45 | 70 | 250 | 3 | 59 | 95.5 |
| 20 | $N_2$ | 40 | 40 | 250 | 3 | 25 | 97 |
| 21 | $N_2$ | 90 | 20 | 220 | 12 | 28.0 | 97 |
| 22 | $N_2$ | 45 | 20 | 220 | 12 | 14.0 | 97 |
| 23 | Ar | 30 | 50 | 220 | 12 | 27 | 97.5 |
| 24 | $CO_2$ | 30 | 50 | 220 | 12 | 29 | 97.5 |

Examples 19–24 illustrate the oxidation of high selectivity cyclic alkenes into ketones using nitrous oxide diluted with inert gas. The contained $N_2O$ in mixture with said inert gas can vary within broad limits, including a region of nitrous oxide concentrations of 25% and less, wherein a possibility of dangerously explosive situations being precluded with any compositions with cyclic alkenes.

The present invention proposes a new method for producing monocyclic ketones $C_7$–$C_{12}$, based on the liquid phase oxidation reaction of monocyclic alkenes with nitrous oxide or its mixture with inert gas. The process provides for a high selectivity involving the target product and blast-resistant work operations and is promising for industrial use.

The invention claimed is:

1. A method for producing monocyclic ketone $C_7$–$C_{20}$ by contacting nitrous oxide with liquid monocyclic alkenes of the formula $C_nH_{2n-2}$ comprising 7–20 carbon atoms on the cycle, at a temperature of 20=350° C. and pressure of $N_2O$ being from 0.01 to 100 atm. in the presence of inert diluent gas.

2. The method of claim 1, wherein the concentration of inert gas in a reaction mixture does not exceed 99%.

3. The method of claim 1, wherein the concentration of inert gas is selected in such a way as to preclude a possibility of dangerously explosive compositions being formed at each and every stage of the process.

4. The method of claim 1, wherein the concentration of inert gas is selected in such a way as to preclude a possibility of dangerously explosive compositions being formed at all stages of the process.

5. The method of claim 1, wherein the reaction is carried out at a temperature of from 20 to 199° C. and a partial pressure of nitrous oxide of from 0.01–100 atm.

6. The method of claim 1, wherein the reaction is carried out at the presence of a catalyst.

7. The method of claim 1, wherein the reaction is carried out in the presence of a solvent.

8. The method of claim 1, wherein the nitrous oxide contains other gases which do not impair process indices.

9. The method of claim 1, wherein the reaction is carried out in a static or flow-type variant.

10. The method of claim 1, wherein recycling gases are used for carrying out the reaction.

* * * * *